US010834032B2

(12) United States Patent
Queva et al.

(10) Patent No.: US 10,834,032 B2
(45) Date of Patent: *Nov. 10, 2020

(54) DETERMINATION OF AN ONLINE COLLABORATION STATUS OF A USER BASED UPON BIOMETRIC AND USER ACTIVITY DATA

(71) Applicant: International Business Machines Corporation, Armonk, NY (US)

(72) Inventors: Stephane Queva, Stepaside (IE); Gaurav Bhagat, Blanchardstown (IE); Damien Murphy, Co. Meath (IE); Fergal Connolly, Saggart (IE)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/447,074

(22) Filed: Jun. 20, 2019

(65) Prior Publication Data

US 2019/0312829 A1    Oct. 10, 2019

Related U.S. Application Data

(63) Continuation of application No. 15/916,488, filed on Mar. 9, 2018.

(51) Int. Cl.
| H04L 12/58 | (2006.01) |
| H04L 29/08 | (2006.01) |
| H04W 4/21 | (2018.01) |
| G06F 3/01 | (2006.01) |

(52) U.S. Cl.
CPC ............ *H04L 51/043* (2013.01); *G06F 3/011* (2013.01); *H04L 51/32* (2013.01); *H04L 67/22* (2013.01); *H04W 4/21* (2018.02); *H04L 51/04* (2013.01)

(58) Field of Classification Search
CPC ......... H04L 67/22; H04L 67/24; H04L 51/32; H04L 51/046; H04L 67/26; H04L 51/043; H04L 51/04; H04B 1/06; A61B 5/1118; G06F 3/011; H04W 4/21
See application file for complete search history.

(56) References Cited

U.S. PATENT DOCUMENTS

| 6,458,080 B1 | 10/2002 | Brown et al. |
| 7,024,369 B1 | 4/2006 | Brown et al. |
| 2007/0143472 A1 | 6/2007 | Clark et al. |

(Continued)

OTHER PUBLICATIONS

List of IBM Patents or Patent Applications Treated as Related, filed Jun. 20, 2019.

*Primary Examiner* — Jungwon Chang
(74) *Attorney, Agent, or Firm* — Will Stock; Edell, Shapiro & Finnan, LLC

(57) ABSTRACT

Methods, systems, and computer readable media are provided for determining a collaboration status of a user of an electronic messaging system based on user data, including: (i) health data representative of a physiological parameter or mental engagement of the user and (ii) collaboration activity data representative of social collaboration activity of the user, to determine the collaboration status. Historical health data and collaboration activity data may be included in the determination of the collaboration status. In some aspects, the collaboration status may reflect a real-time collaboration status of the user.

12 Claims, 8 Drawing Sheets

(56) References Cited

U.S. PATENT DOCUMENTS

| | | | |
|---|---|---|---|
| 2010/0299615 A1* | 11/2010 | Miluzzo | H04L 67/24 |
| | | | 715/752 |
| 2012/0289789 A1 | 11/2012 | Jain et al. | |
| 2013/0217350 A1* | 8/2013 | Singh | H04B 1/06 |
| | | | 455/130 |
| 2014/0164611 A1 | 6/2014 | Molettiere et al. | |
| 2014/0240122 A1* | 8/2014 | Roberts | G16H 40/63 |
| | | | 340/539.11 |
| 2017/0124520 A1 | 5/2017 | Chakra et al. | |
| 2017/0135635 A1 | 5/2017 | Bostick et al. | |
| 2017/0277854 A1 | 9/2017 | Kelly et al. | |
| 2018/0081778 A1 | 3/2018 | Terho et al. | |
| 2018/0285827 A1 | 10/2018 | Dotan-Cohen et al. | |
| 2019/0141190 A1* | 5/2019 | Gupta | H04M 3/4936 |
| 2019/0205839 A1* | 7/2019 | Dotan-Cohen | A61B 5/1118 |
| 2019/0280993 A1* | 9/2019 | Queva | H04W 4/21 |

\* cited by examiner

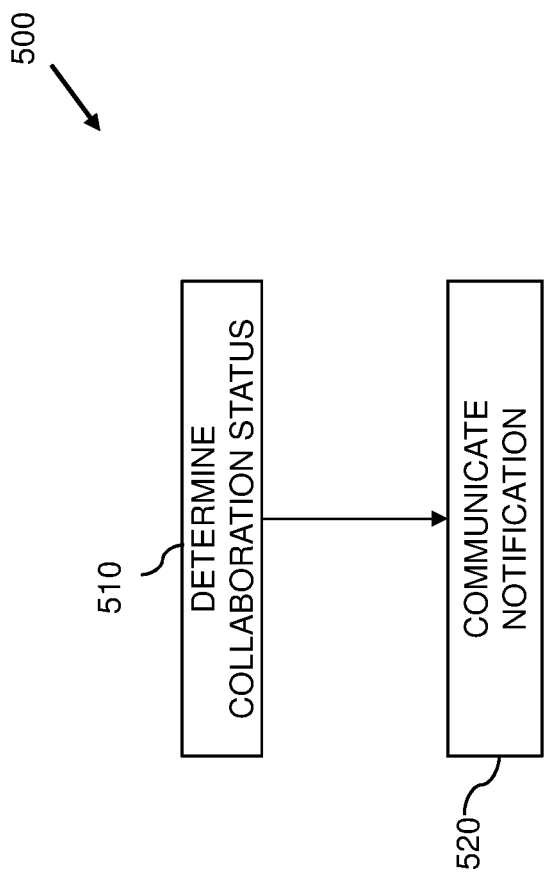

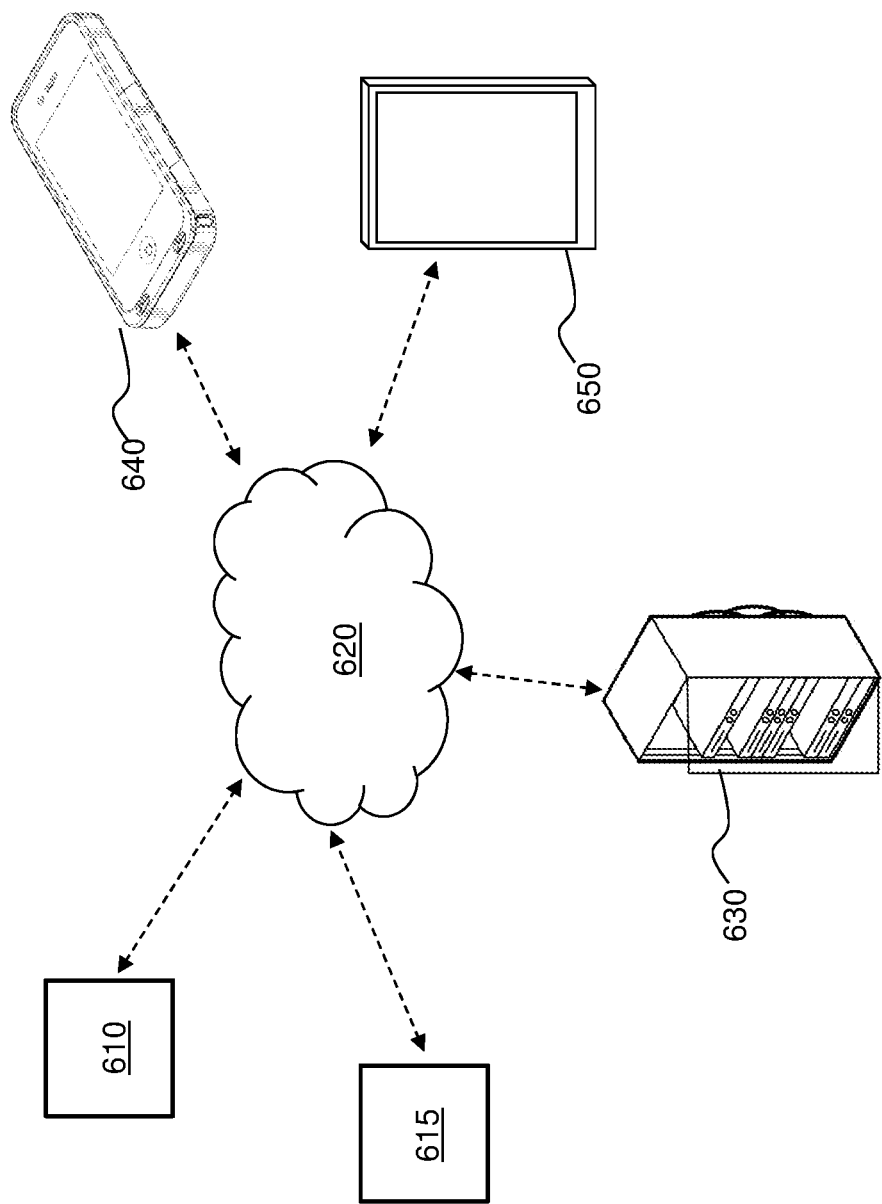

DETERMINATION OF AN ONLINE COLLABORATION STATUS OF A USER BASED UPON BIOMETRIC AND USER ACTIVITY DATA

BACKGROUND

1. Technical Field

Present invention embodiments relate to determining a collaboration status of a user of an electronic messaging system, and more specifically, to controlling user status notifications of an electronic messaging system based on a determined collaboration status of the user.

2. Discussion of the Related Art

The use of computing devices and communication networks to exchange information in the form of electronic messages is widely known. Typically, a user at a personal computing device can utilize a messaging application to communicate with another user at another personal computing device via a communication network. For example, an instant messaging service provider provides users with a client side application that allows one user to communicate with another user over a network in real time. An instant messaging display interface is presented to each user and enables users to establish relationships with other users and to engage in chats with other users.

It is also known for messaging applications to enable a user to specify a collaboration status, which may otherwise be thought of as an 'availability status' or 'presence status'. Such a collaboration status typically indicates whether a user is available, able or willing to communicate with other users (i.e. collaborate with other users). A user typically enters or selects a status from a list of possible options. Due to such reliance on a user action to select an appropriate status and/or frequently change a status (e.g., to reflect changes in circumstances), it is common for such a user-entered/selected status to be inaccurate or out-of-date.

SUMMARY

According to embodiments of the present invention, a method for determining a collaboration status of a user of an electronic messaging system is provided.

In further embodiments, a method for controlling user status notifications of an electronic messaging system, wherein the method is based on a determined collaboration status of a user of an electronic messaging system is provided. A computer program product including computer program code for implementing such a proposed method when executed on a processor of a data processing system is also provided, and an electronic messaging system configured to execute this computer program code is provided.

In still other embodiments, a system for determining a level of interest of a user in a topic of a thread of an electronic messaging system is provided.

In yet other embodiments, a system for determining a collaboration status of a user of an electronic messaging system is provided.

According to embodiments of the present invention, a computer-implemented method for determining a collaboration status of a user of an electronic messaging system is provided. The method comprises obtaining health data representative of a physiological parameter or physical activity of the user. The method also comprises obtaining collaboration activity data representative of social collaboration activity of the user. The method then comprises determining a collaboration status of the user based on the obtained health data and the obtained social collaboration activity data.

According to embodiments of the present invention, there is provided a computer-implemented method for controlling user status notifications of an electronic messaging system. The method comprises determining a collaboration status of a user of an electronic messaging system according to a proposed embodiment. The method also comprises controlling communication of a notification associated with the user based on the determined collaboration status of the user.

According to another aspect of the invention, there is provided a computer program product for determining a collaboration status of a user of an electronic messaging system. The computer program product comprises a computer readable storage medium having program instructions embodied therewith, the program instructions executable by a processing unit to cause the processing unit to perform a method according to an embodiment of the invention.

According to another aspect of the invention, there is provided an electronic messaging system comprising at least one processor and the computer program product according to an embodiment. The at least one processor is configured to execute the computer program code of said computer program product.

According to yet another aspect of the invention, there is provided a system for determining a collaboration status of a user of an electronic messaging system. The system comprises an interface configured to obtain health data representative of a physiological parameter or physical activity of the user and to obtain collaboration activity data representative of social collaboration activity of the user. The system also comprises a processing unit configured to determine a collaboration status of the user based on the health data and the social collaboration activity data obtained by the interface.

According to yet other aspects of the invention, there is provided a system for controlling user status notifications of an electronic messaging system. The system comprises a system for determining a collaboration status of a user of an electronic messaging system according to an embodiment. The system also comprises a controller configured to control communication of a notification associated with the user based on the determined collaboration status of the user.

BRIEF DESCRIPTION OF THE DRAWINGS

Embodiments of the present invention will now be described, by way of example only, with reference to the following drawings, in which:

FIG. 5 is a simplified flow diagram of a method for controlling user status notifications of an electronic messaging system;

FIG. 6 is an example computing environment for monitoring collaboration status of a user of an electronic messaging system according to an embodiment.

DETAILED DESCRIPTION

Figure 1:
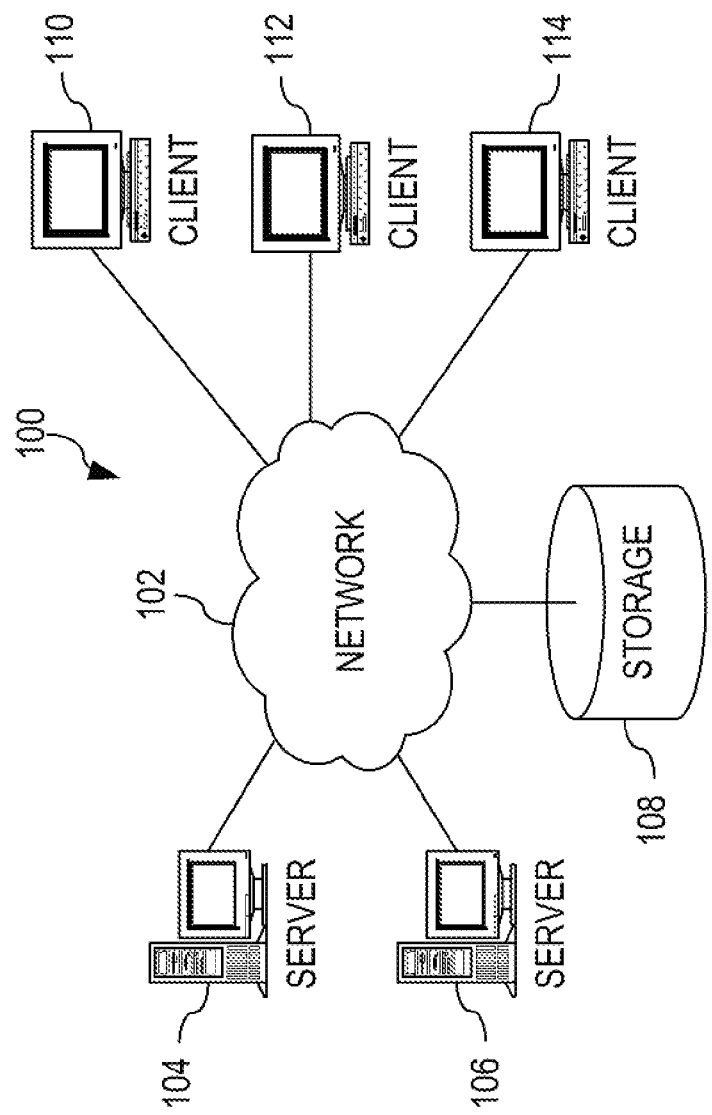
FIG. 1 depicts a pictorial representation of an example distributed system in which aspects of the illustrative embodiments may be implemented.

It should be understood that the Figures are merely schematic and are not drawn to scale. It should also be understood that the same reference numerals are used throughout the Figures to indicate the same or similar parts.

In the context of the present application, where embodiments of the present invention constitute a method, it should be understood that such a method is a process for execution by a computer, i.e. a computer-implementable method. The various steps of the method therefore reflect various parts of a computer program, e.g., various parts of one or more algorithms.

Also, in the context of the present application, a system may be a single device or a collection of distributed devices that are configured to execute one or more embodiments of the methods of the present invention. For instance, a system may be a personal computer (PC), a server or a collection of PCs and/or servers connected via a network such as a local area network, the Internet and so on to cooperatively execute at least one embodiment of the methods of the present invention.

Methods for determining a collaboration status of a user of an electronic messaging system are provided. Also, methods for controlling user status notifications of an electronic messaging system based on a determined collaboration status of a user are provided.

Proposed embodiments may utilize information representative of the physical and/or mental engagement of a user and information about the user's collaboration activities (such as work and messaging activities) so as to provide techniques for determining a collaboration status of the user. Proposed approaches to identifying a collaboration status of the user are thus enabled due to the context of a user's health and work activity.

For example, embodiments propose to determine an indicator of a user's health or well-being based on his/her collaboration activities (e.g., a number of electronic messages typed, sent or received; a number of messaging system interactions; a number of meetings attended; hours spent in meetings; a distance traveled for the meetings; etc.) during a specified time interval (e.g., during a calendar day) and measurements of a physiological parameter or physical activity of the user. Combining data captured by health monitors with data about collaboration activity may provide insight into user's health or well-being, and this may then be used to determine whether the user should be indicated as being available or unavailable to communicate with other users via an electronic messaging system. For example, if a user currently has a high heart rate or has done a high number of steps during the day and the user has managed a high collaboration workload during the day (as may be indicated by collaboration activity data), embodiments may be configured to determine that the user should only be contacted in case of urgent situations. Such a collaboration status as determined by an embodiment may be indicated, for example, using a graphic symbol comprising a either colour of red, amber or green, wherein red is used to indicate an 'unavailable' collaboration status, amber is used to indicate an 'only available for urgent maters' collaboration status, and green is used to indicated an 'available' collaboration status.

Thus, it is proposed to combine information about a user's physical and/or mental status (e.g., obtained from measurements of physiological parameters and/or physical activity, such as heart rate, blood pressure, steps taken, cortisol levels, hours slept, etc.) with information about a user's social collaboration activity (e.g., number of messages sent and/or read, number of meetings attended, etc.) to determine an availability status which not only accounts for a user's current health but also accounts for how busy and/or stressed the user may be due to his/her collaboration activities. This may provide a more accurate or appropriate indicator of a user's collaboration status, for example by considering his/her well-being in view of recent heath status and collaboration activities. Embodiments may therefore protect a user's health or well-being from being negatively impacted or influenced by determining his/her collaboration status to be 'unavailable', so as to prevent further collaboration activities being invited via an electronic messaging system when the user has high blood pressure and has exhibited a high-level of social collaboration activity for example.

In particular, it is proposed that a user's collaboration status may be determined based on his/her physical health and mental engagement or status and how active or busy he/she has been on an electronic messaging system for example. By accounting for both user health and user work/collaboration activity, proposed embodiments may take into account user health in the context of user work/collaboration activity so as to gauge whether health readings or work/collaboration activities should allow, invite or prevent further collaboration via an electronic messaging system. In this way, more accurate or appropriate assessment of a user's collaboration status may be provided.

For example, obtained health data may show that a user's heart rate is in a normal/healthy range and blood pressure is only slightly higher than a normal/healthy range, and so simplistic approaches may (incorrectly) infer that the user is available and willing to collaborate via an electronic messaging system. However, by taking a context-based approach and using collaboration activity data to identify that the user has attended a high-number of lengthy meetings in the preceding few hours (e.g., during the morning of a current day), proposed embodiments can obtain a better understanding of the likelihood that the user would prefer not to be (or may benefit from not being) available and willing to collaborate via an electronic messaging system.

Collaboration activity data representative of social collaboration of a user may be captured from many different sources. Embodiments may thus obtain overall collaboration activity of the user from a wide range of collaboration tools (e.g., instant messaging applications, e-mails applications, calendar applications, personal organization apps, etc.). Similarly heath data representative of a physiological parameter or physical/mental activity of a user may be captured from many different sources or sensors. Embodiments may thus obtain overall health data of the user from a wide range of health monitoring tools or sensors (e.g., activity tracking apps and system, heart monitors, blood pressure monitors, hormone monitors, sleep tracking devices/systems, etc.).

Some embodiments may also obtain historical health data relating to a pattern or trend of previously obtained measurements of a physiological parameter or physical activity for the user. A collaboration status of the user may then be determined further based on such obtained historical health data. Furthermore, such a collaboration status may be associated with a future time or date based on the obtained historical health data. In this way, a prediction (i.e. an indication for a time or date in the future) of user health may be obtained based on historic and current health data captured for the user. Determinations as to a user's collaboration status at a future point in time may thus be provided by proposed embodiments, and this may be particularly advantageous for planning and/or managing collaboration and communication workloads in an electronic messaging system. For example, such embodiments may identify recurring weekly or monthly meetings, and may automatically assign a collaboration status for these recurring events.

By way of example, the physiological parameter or physical activity of the user may comprise one or more of: heart rate; blood pressure; cortisol and/or other hormone level, body temperature; pulse-oximetry; mood; steps taken; and distance walked. A wide range of health status indicators may therefore be employed by embodiments to infer a physical and/or mental status of the user, and these may be obtained from one or more conventional monitors or sensors. Existing health monitoring apparatus that may be cheap and/or widely available may thus be employed in conjunction with proposed embodiments, thereby potentially minimizing or reducing cost and/or complexity.

In embodiments, the social collaboration activity of the user may comprise one or more of: number of meetings attended during a predetermined time period; time spent in meetings during a predetermined time period; distance traveled during a predetermined time period; number of messages sent using the electronic messaging system during a predetermined time period; number of words typed in message(s) sent using the electronic messaging system during a predetermined time period; number of active parallel discussions using the electronic messaging system; number of open draft message(s) or emails; and number of unread electronic messages or emails; number of comments or articles submitted to an online community (e.g., webpage, online forum, messageboard, etc.) during a predetermined time period. Embodiments may therefore obtain collaboration activity data from many different sources, including a wide range of collaboration tools (e.g., instant messaging applications, e-mails applications, calendar applications, personal organization apps, etc.). Existing collaboration tools, programs, systems and applications that may be cheap and/or widely available may thus be leveraged in conjunction with proposed embodiments.

Some embodiments may obtain historical collaboration activity data relating to a pattern or trend of previously obtained measurements of social collaboration activity of the user. Determining a collaboration status of the user may then be further based on the obtained historical collaboration activity data. Furthermore, the collaboration status may be associated with a future time or date based on the obtained historical collaboration activity data. In this way, a prediction (i.e. an indication for a time or date in the future) of user health may be obtained based on historic and current collaboration activity data captured for the user. Activity-based determinations as to a user's collaboration status at a future point in time may thus be provided by proposed embodiments, and this may be particularly advantageous for planning and/or managing collaboration and communication workloads in an electronic messaging system.

In another example, an embodiment may obtain a user input representative of a current or future collaboration status of the user. A collaboration status of the user may then be determined further based on the obtained user input. For example, a user may automatically adjust the determination processes so as to account for user preference or circumstances. One such example may comprise the user providing an input that over-rides (i.e. takes precedence over) a health indicator (e.g., measurement of a physiological parameter) so as to more reflect how the user feels.

Some embodiments may be configured to obtain a message of user communicated by the electronic messaging system and to analyze the message to identify an indicator of status of the user. A collaboration status of the user may then be determined further based on the identified indicator of status of the user. Predictive user health indication may thus be provided by taking account of information provided in messages communicated by the user via the electronic messaging system. For instance, an embodiment may identify that a message sent by the user contains the expression "I am busy" in relation to a specific time interval, and this information may be used when determining the user's collaboration status for that time interval. By way of further example, some embodiments may further determine a time or date associated with the identified indicator of status of the user, and then determining a collaboration status of the user may be further based on the determining a time or date associated with the identified indicator of status of the user. Embodiments may thus analyze messages communicated by the user in order to identify information that may be useful for determining the user's current or future collaboration status. Utilising widely-available text analysis capabilities, embodiments may monitor messages that the user may be sending or receiving, and then this may be utilized in the process of determining a collaboration status of the user.

Embodiments may also provide techniques for controlling the communication of a user status notification of a messaging system based on a determined collaboration status of the user. Proposed embodiments for determining a collaboration status of the user of an electronic messaging system may therefore be employed for the purpose of controlling status notifications in the messaging system.

An embodiment may be further configured to generate a display control signal for modifying a graphical element (such as a user status notification) based on the determined collaboration status of a user, and the system may further comprise: a display system configured to display the graphical element in accordance with the generated display control signal. In this way, a second user may have an appropriately arranged display system that can receive and display information about a determined collaboration status of a first user, and the second user may be remotely located from the first user. Embodiments may therefore enable a second user to remotely identify and/or monitor the collaboration status of a first user of an electronic messaging system using a portable display device, such as a laptop, tablet computer, mobile phone, PDA, etc.

It will be appreciated that all or part of a system according to an embodiment may comprise one or more data processing units. For example, the processing unit may be implemented using a single processor which is configured to undertake data processing in order to determine a collaboration status of a user (based on obtained health data and collaboration activity data). The processing unit may be remotely located from the sensors or apparatus used to obtain the health data and/or the collaboration activity data, and data obtained by the sensors/apparatus may be communicated to the signal processing unit via respective communication links.

The system may further comprise: a server device comprising the processing unit. Dedicated data processing means may therefore be employed for the purpose of determining a collaboration status of the user, thus reducing processing requirements or capabilities of other components or devices of the system.

The system may further comprise a client device, wherein the client device comprises the processing unit and a display system. In other words, a second user may have an appropriately arranged client device (such as a laptop, tablet computer, mobile phone, PDA, etc.) which processes received signals in order to determine a collaboration status of a user of an electronic messaging system.

Thus, processing may be hosted at a different location from where the health data and/or collaboration status data are generated or issued. For example, for reasons of power efficiency (e.g., to improve battery lifetime) it might be advantageous to execute only part of the processing at a sensor location(s), thereby reducing associated costs, processing power, transmission requirements, etc.

Embodiments may also enable some of the processing load to be distributed throughout the system. For example, pre-processing may be undertaken at a sensor system. Alternatively, or additionally, processing could be undertaken at a communication gateway. In some embodiments, processing may be undertaken at a remote gateway or sever, thus relinquishing processing requirements from an end-user or output device. Such distribution of processing and/or hardware may allow for improved maintenance abilities (e.g., by centralising complex or expensive hardware in a preferred location). It may also enable computational load and/or traffic to be designed or located within a networked system according to the processing capabilities available. A preferable approach may be to process sensor signals locally and transmit extracted data for full processing at a remote server.

Thus, it will be understood that processing capabilities may be distributed throughout the system in different ways according to predetermined constraints and/or availability of processing resources.

By way of further example, embodiments may propose extensions to an electronic messaging system. Such extensions may provide for effective (e.g., more accurate or appropriate) user status notifications to be provided. In this way, a user's collaboration status may be automatically and dynamically maintained. Embodiments may therefore be used in combination with conventional electronic messaging systems to provide improved user status capabilities.

Illustrative embodiments may therefore provide techniques for controlling user status notifications of an electronic messaging system. Automatic and/or dynamic user collaboration status (i.e. user availability status) generation techniques may therefore be provided by proposed embodiments.

Modifications and additional steps to a traditional electronic messaging system may also be proposed which may enhance the value and utility of the proposed techniques.

Figure 2:
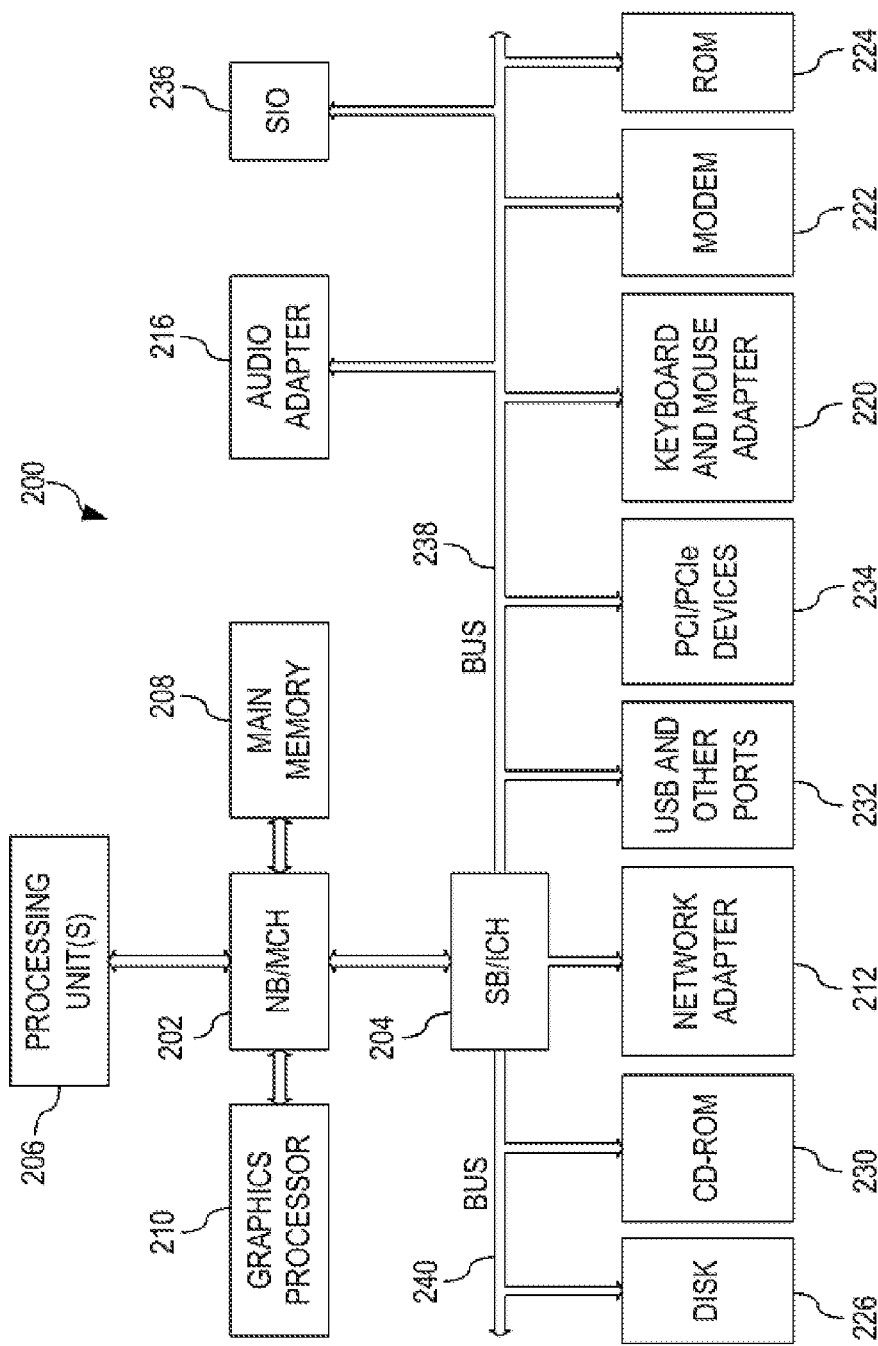
FIG. 2 is a block diagram of an example system in which aspects of the illustrative embodiments may be implemented.

Illustrative embodiments may be utilized in many different types of messaging environments. In order to provide a context for the description of elements and functionality of the illustrative embodiments, FIGS. 1, 2 and 6 are provided hereafter as example environments in which aspects of the illustrative embodiments may be implemented. It should be appreciated that FIGS. 1, 2 and 6 are only examples and are not intended to assert or imply any limitation with regard to the environments in which aspects or embodiments of the present invention may be implemented. Many modifications to the depicted environments may be made without departing from the scope of the present invention.

Proposed techniques may provide other collaboration tool users (e.g., other users of an electronic messaging system) with information that is indicative of the collaboration status (i.e. availability status) of a given user, and such information may be reflective of the health, well-being or stress of the given user. The collaboration status may comprise information having two parts: (i) a real-time (or current) indication of collaboration status; and (ii) a prediction of future collaboration status.

FIG. 1 depicts a pictorial representation of an example distributed messaging system in which aspects of the illustrative embodiments may be implemented. Distributed system 100 may include a network of computers in which aspects of the illustrative embodiments may be implemented. The distributed system 100 contains at least one network 102, which is the medium used to provide communication links between various devices and computers connected together within the distributed data processing system 100. The network 102 may include connections, such as wire, wireless communication links, or fiber optic cables.

In the depicted example, a first 104 and second 106 servers are connected to the network 102 along with a storage unit 108. In addition, clients 110, 112, and 114 are also connected to the network 102. The clients 110, 112, and 114 may be, for example, personal computers, network computers, or the like. In the depicted example, the first server 104 provides data, such as boot files, operating system images, and applications to the clients 110, 112, and 114. Clients 110, 112, and 114 are clients to the first server 104 in the depicted example. The distributed system 100 may include additional servers, clients, and other devices not shown.

In the depicted example, the distributed system 100 is the Internet with the network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the present invention, and therefore, the particular elements shown in FIG. 1 should not be considered limiting with regard to the environments in which the illustrative embodiments of the present invention may be implemented.

FIG. 2 is a block diagram of an example system 200 in which aspects of the illustrative embodiments may be implemented. The system 200 is an example of a computer, such as client 110 in FIG. 1, in which computer usable code or instructions implementing the processes for illustrative embodiments of the present invention may be located.

In the depicted example, the system 200 employs a hub architecture including a north bridge and memory controller hub (NB/MCH) 202 and a south bridge and input/output (I/O) controller hub (SB/ICH) 204. A processing unit 206, a main memory 208, and a graphics processor 210 are connected to NB/MCH 202. The graphics processor 210 may be connected to the NB/MCH 202 through an accelerated graphics port (AGP).

In the depicted example, a local area network (LAN) adapter 212 connects to SB/ICH 204. An audio adapter 216, a keyboard and a mouse adapter 220, a modem 222, a read only memory (ROM) 224, a hard disk drive (HDD) 226, a CD-ROM drive 230, a universal serial bus (USB) ports and other communication ports 232, and PCI/PCIe devices 234 connect to the SB/ICH 204 through first bus 238 and second bus 240. PCI/PCIe devices may include, for example, Ethernet adapters, add-in cards, and PC cards for notebook computers. Typically, PCI uses a card bus controller, while PCIe does not. ROM 224 may be, for example, a flash basic input/output system (BIOS).

The HDD 226 and CD-ROM drive 230 connect to the SB/ICH 204 through second bus 240. The HDD 226 and CD-ROM drive 230 may use, for example, an integrated drive electronics (IDE) or a serial advanced technology attachment (SATA) interface. Super I/O (SIO) device 236 may be connected to SB/ICH 204.

An operating system runs on the processing unit 206. The operating system coordinates and provides control of various components within the system 200 in FIG. 2. As a client, the operating system may be a commercially available operating system. An object-oriented programming system, such as the Java™ programming system, may run in conjunction with the operating system and provides calls to the operating system from Java™ programs or applications executing on system 200.

As a server, system 200 may be, for example, an IBM® eServer™ System p® computer system, running the Advanced Interactive Executive (AIX®) operating system or the LINUX® operating system. The system 200 may be a symmetric multiprocessor (SMP) system including a plurality of processors in processing unit 206. Alternatively, a single processor system may be employed.

Instructions for the operating system, the programming system, and applications or programs are located on storage devices, such as HDD 226, and may be loaded into main memory 208 for execution by processing unit 206. Similarly, one or more message processing programs according to an embodiment may be configured to be stored by the storage devices and/or the main memory 208.

The processes for illustrative embodiments of the present invention may be performed by processing unit 206 using computer usable program code, which may be located in a memory such as, for example, main memory 208, ROM 224, or in one or more peripheral devices 226 and 230.

A bus system, such as first bus 238 or second bus 240 as shown in FIG. 2, may comprise one or more buses. Of course, the bus system may be implemented using any type of communication fabric or architecture that provides for a transfer of data between different components or devices attached to the fabric or architecture. A communication unit, such as the modem 222 or the network adapter 212 of FIG. 2, may include one or more devices used to transmit and receive data. A memory may be, for example, main memory 208, ROM 224, or a cache such as found in NB/MCH 202 in FIG. 2.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the system mentioned previously, without departing from the spirit and scope of the present invention.

Moreover, the system 200 may take the form of any of a number of different data processing systems including client computing devices, server computing devices, a tablet computer, laptop computer, telephone or other communication device, a personal digital assistant (PDA), or the like. In some illustrative examples, the system 200 may be a portable computing device that is configured with flash memory to provide non-volatile memory for storing operating system files and/or user-generated data, for example. Thus, the system 200 may essentially be any known or later-developed data processing system without architectural limitation.

In some aspects, a collaboration status determination process may be enhanced by accounting for factors which may impact a user's well-being but not be directly detectible via monitoring of physiological parameters of the user. For example, methods may account for recent collaboration activities or workload to identify where a user's stress-levels or mood may be indicative of potential overwork if the user then uses an electronic messaging system. In example implementations, data from health monitors is combined with data from collaboration tools/applications to identify whether or not a user should be indicated as being available on an electronic messaging system. By accounting not only for the values of a user's physiological parameters but also a recent workload or collaboration activity of the user, proposed embodiments may provide a more appropriate indication of collaboration status which account for a user's well-being or stress.

Figure 3:
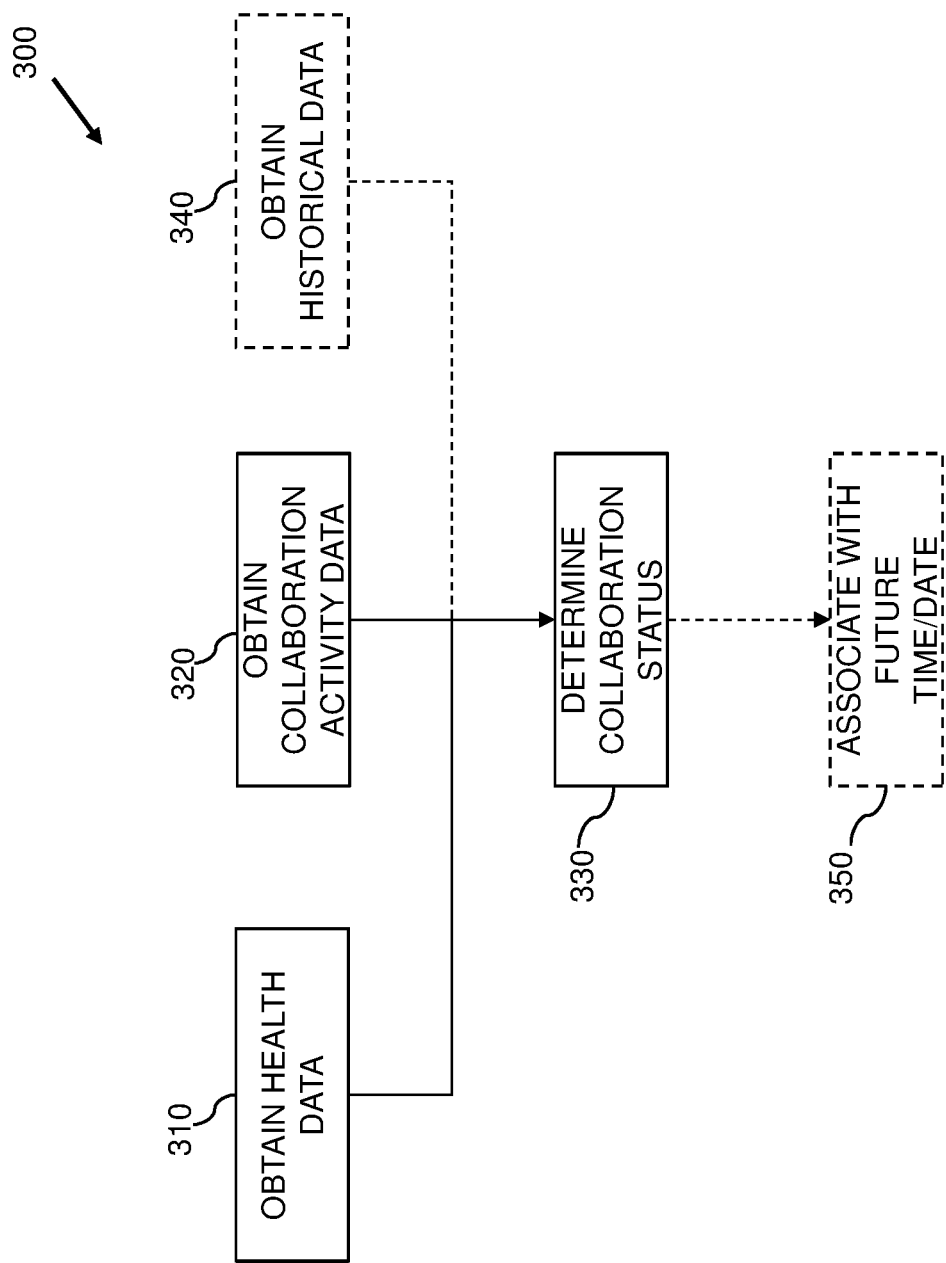
FIG. 3 is a simplified flow diagram of a method of determining a collaboration status of a user of an electronic messaging system according to an embodiment.

Referring now to FIG. 3, a flow diagram of a method 300 of determining a collaboration status of a user of an electronic messaging system is depicted according to an embodiment. Here, the electronic messaging system implements an instant messaging application or service which is configured to interface with multiple users.

The method comprises step 310 of obtaining health data representative of a physiological parameter or physical activity of the user. By way of example, the physiological parameter or physical activity of the user comprises at least one of: heart rate; blood pressure; body temperature; pulse-oximetry; mood; steps taken; and distance walked. Health data may therefore be obtained by receiving one or more signals from health monitoring apparatus and/or sensors worn or carried by the user.

The method also comprises step 320 of obtaining collaboration activity data representative of social collaboration activity of the user. For example, the social collaboration activity of the user may comprise at least one of: number of meeting attended during a predetermined time period; time spent in meetings during a predetermined time period; distance traveled during a predetermined time period; number of messages sent using the electronic messaging system during a predetermined time period; number of words typed in messages sent using the electronic messaging system during a predetermined time period; number of active parallel discussions using the electronic messaging system; number of open draft messages or emails; and number of unread electronic messages or emails. Collaboration activity data may therefore be obtained from a wide range of collaboration tools (such as instant messaging applications, e-mails applications, calendar applications, personal organization apps, etc.) and provide information regarding a user's work or socializing activities. From such information, one or more clues or signs of the user's mindset, well-being or stress level may be inferred.

The method then proceeds to step 330 of determining a collaboration status of the user based on the obtained health data and the obtained social collaboration activity data.

Thus, step 330 determines a status of the user as a function of the health and activity indicators of the user, namely physical health parameters of the user and collaboration activity of the user.

By way of example, detected blood pressure and/or heart rate of the user can provide a relatively straightforward indication of a level of stress or overwork of the user. However, such physiological parameters alone may not provide a complete picture of a user's state of well-being, stress and/or tiredness for example. For this reason, the proposed embodiment may also include user information about the social collaboration activity of the user to provide an improved context for determining a user's state of well-being, stress and/or tiredness. For instance, obtained health data for a user may indicate that the user's heart rate is within in a normal, healthy range, but obtained social collaboration activity data may indicate that the user has spent all morning in various meetings without any breaks (i.e. rest periods). Thus, unlike simplistic approaches which may incorrectly employ only the obtained health data to infer that the user is in good health and thus available and willing to receive messages via the electronic messaging system, step 330 of the proposed embodiment can use the obtained social collaboration data and infer that the user may be tired and unwilling to receive messages via the electronic messaging system.

In some aspects, the collaboration status may be an ongoing, real-time measure of the availability of the user. By collecting and analyzing health data which may include biometric data from sensors (e.g., wearable sensors, including heart rate monitors, blood pressure monitors, EEG sensors, etc.) on an ongoing basis, as well as collaboration activity data, the collaboration status of the user can be continuously updated. In some cases, the collaboration status may be updated in real-time, e.g., by analyzing the collected data within milliseconds.

In some aspects, the systems and methods presented herein may perform an action in response to a change in a collaboration status of a user. For example, the system may deny online messaging access of others to the user, e.g., when the collaboration status of the user changes to unavailable. A message or other indication may automatically be provided to denied personnel indicating that the user is not available, and thereby, reducing the workload of the user.

The methods and systems presented herein provide improvements over prior techniques as they do not require a user to perform an action (or an ongoing series of actions) to update their collaboration status. Prior systems generally rely on a user to enter a change to an availability setting in order to change their collaboration status, and if a user neglects to perform such an activity, their respective collaboration status does not become updated. Processes involving manually updating a collaboration status are not only less accurate (as they are not real-time) but also increase the workload of the user. In contrast, present techniques reduce the workload of the user not only by updating their respective collaboration status automatically, but also by limiting availability of the user to other personnel, thereby reducing the number of distractions to the user during times of stress to improve productivity. Accordingly, present techniques provide a way to dynamically adjust a collaboration status reflecting a user's availability/access in an automated manner.

A further example may also include the additional step 340 of obtaining historical data. Such historical data may relate to a pattern or trend of: previously obtained measurements of a physiological parameter or physical activity for the user; and/or previously obtained measurements of social collaboration activity of the user. The step 330 of determining a collaboration status of the user may then be further based on the obtained historical data. Furthermore, such embodiments may also comprise an additional step 350 of associating the collaboration status with a future time or date based on the obtained historical health data. For instance, based on an identified pattern or trend in a physiological parameter and/or social collaboration activity, future values of the physiological parameter and/or social collaboration activity can be determined and then used to determine a collaboration status for the future time(s), and the predicted future collaboration status(es) can be associated with the future times and/or dates.

Also, it will be appreciated that, although the embodiment of FIG. 3 has been described as employing particular processes and step, other processes or methodologies for detecting a collaboration status of a user may be employed.

Figure 4A:
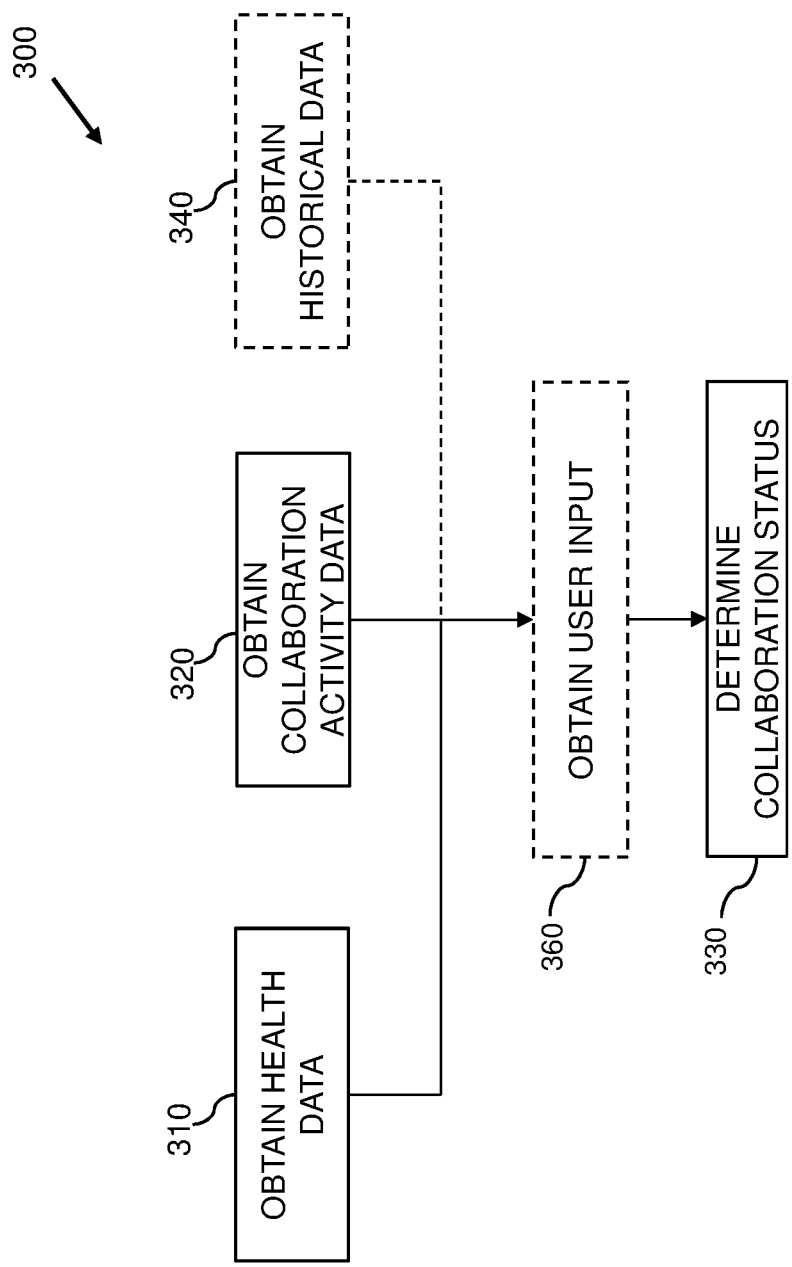
FIG. 4A is a flow diagram depicting a modification to the embodiment of FIG. 3.

For example, FIG. 4A depicts a modification to the embodiment of FIG. 3. More specifically, the method according to the embodiment of FIG. 4A comprises an additional step (step 360) of obtaining a user input representative of a current or future collaboration status of the user. The step 330 of determining a collaboration status of the user is then further based on the obtained user input. For instance, in step 360, the user input may comprise information provided by the user regarding his/her mood, stress level or other indication of general well-being. This user defined information may be used to provide further context and detail regarding the user's suitability or availability to use the electronic messaging system.

Figure 4B:
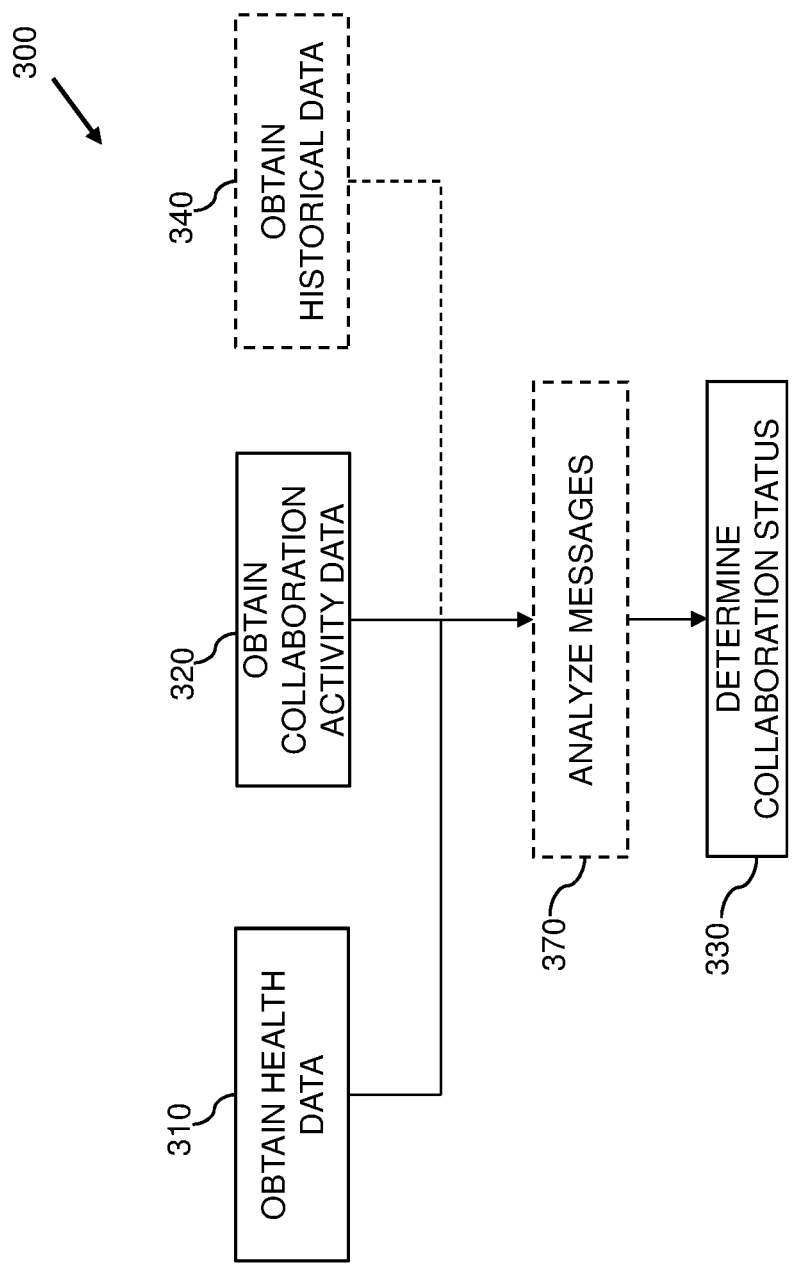
FIG. 4B is a flow diagram depicting an alternative modification to the embodiment of FIG. 3.

In yet another example, FIG. 4B depicts a different modification to the embodiment of FIG. 3. More specifically, the method according to the embodiment of FIG. 4B comprises an additional step (step 370) of obtaining and analyzing messages of a user communicated by the electronic messaging system to identify an indicator of status of the user. The step 300 of determining a collaboration status of the user is then further based on the identified indicator of status of the user. For instance, the text content of a message sent by the user may be parsed and an expression such as "I am busy today" may be identified. Identification of such and expression may then be used in step 330 to determine that the user will not be available and/or wish to be identified as 'available' on the electronic messaging system, and this may take precedence over a determination of collaboration status made only using the health data and collaboration data. It will therefore be appreciated that the method include determining a time or date associated with the identified indicator of status of the user (such as 'this afternoon' in the abovementioned example). The determined collaboration status of the user may then be associated with a date and/or time (e.g., associated with the afternoon of the current day for the abovementioned example).

From the above description, it will be appreciated that methods of using both information from health monitoring sensors (e.g., heart rate monitors) and collaboration systems/applications (e.g., instant messaging applications, electronic mail systems, social media applications, etc.) as a way of providing an indication of the user's availability, suitability and/or willingness to use an electronic messaging system. This can be implemented on a conversation-by-conversation basis, and/or utilized across multiple threads of discussions in the electronic messaging system. For instance, different collaboration status values may be determined for different discussions or group chats according to their relative importance, age, participants, topic(s), etc. Where the health data indicates that the user is healthy and well, but the collaboration activity data indicates that the user has been very busy, an embodiment may determine a collaboration status of "available" on the electronic messaging system for selected high priority users (e.g., managers, executives, senior staff, etc.), whereas a collaboration status of "busy" or "unavailable" may be determined and indicated to lower priority users.

Thus, it will be understood that an indication of a user's current health or well-being may be determined by embodiments. Such determination may, for example, be based on: (i) a number of meetings attending during a specified past period of time (e.g., single working day); (ii) a number of hours spent in meetings during a specified period of time (e.g., single working day); (iii) a distance traveled to attend different meetings; (iv) a number of instant messaging discussions completed during a time period; (v) a number of words typed during a predetermined time period; (vi) a number of posts (including comments) on community-based portals (e.g., social media); (vii) a number of parallel conversations being managed at once on a collaboration application; (viii) a number of open draft e-mails; (ix) a number of unread e-mails received over a predetermined time period (e.g., preceding 24 hours); and/or (x) data captured from health and activity tracking devices (e.g., heart rate, steps . . . ).

Also, proposed embodiments may provide techniques for predicting a user's health or well-being based on based on historic data and current data. Such historic data may, for example, comprise information relating to: (i) a number of meetings a user typically attends; (ii) a number of meetings a user plans to attend in a predetermined time period; (iii) a number of hours a user typically spends in meetings; (iv) a distance a user will be traveling to attend scheduled/planned meetings; (v) a number of instant messaging discussions typically completed during a time period (e.g., day, week or year); (vi) a number of words typically typed in messaging discussions in a time period; and/or (vii) data captured from health and activity tracking devices (e.g., heart rate, steps, etc.) during a time period.

By way of example, a collaboration status may be automatically calculated and may be shown either as a percentage (%), a Red/Amber/Green (RAG) indicator, or a combination of both. Parameters or data used for the determination of collaboration status may be associated with respective weightings and/or threshold values. Also, a user may override one or more values with custom values.

There may also be provided a technique for controlling the communication of an indicator or notification of collaboration status (e.g., availability) of a user of an electronic messaging system based on a determined collaboration status of the user. Thus, proposed embodiments of determining a collaboration status of a user of an electronic messaging system may be employed for the purpose of controlling messages or notifications in the messaging system. For instance, a notification or message may be controlled so that it is only communicated to a user if the user's collaboration status has been determined to be 'available' or 'ready'. In this way, notifications or messages may be automatically filtered or controlled according to a user's determined collaboration status, thereby reducing or avoiding the provision of nuisance or distracting notifications when a user's well-being is reduced and/or stress-levels are elevated.

Embodiments may therefore be provided as extensions to existing electronic messaging systems. Such extensions may provide for more effective status indications and/or improved message filtering capabilities. In this way, a user may not be overwhelmed, interrupted or overworked when his/her health and/or activity is such that use of the electronic messaging system may be detrimental to his/her health or well-being.

Referring now to FIG. 5, there is depicted a flow diagram of a proposed method 500 for controlling user status notifications of an electronic messaging system. The method 500 begins with the step 510 of determining a collaboration status of a user of the electronic messaging system, and comprises the method 300 described above with reference to FIG. 3.

Next, in step 520, communication of a notification associated with the user is controlled based on the determined collaboration status of the user. More specifically, a notification is communicated to other users of the electronic messaging system which indicates the determined collaboration status. This may, for instance, employ a process of translating the collaboration status to one of an available set of possible status identifiers which provide for quick and easy understanding of a user's collaboration status. For example, a determined collaboration status may be communicated using one of three available colors such as green, amber or red, where green indicates a user is available, amber indicates a user is only available for urgent matters, and red indicates the user is unavailable.

It is also noted that, in some embodiments, the method 500 may further comprise a step of obtaining historical information relating to a previously determined collaboration status of the user (e.g., from a database). The step 520 of controlling communication of the notification associated with the user may then be further based on the obtained historical information. In this way, previously obtained information about a user's collaboration status can be used, thus facilitating an improved (e.g., more accurate) assessment of the user's collaboration status and whether to communicate a notification to other users.

From the description provided above, it will be understood that proposed embodiments may utilize the nature and/or characteristics of user collaboration activity (such a meeting activity, messaging activity, e-mail activity, etc.) in combination with monitored physiological parameters so as to provide techniques for determining a collaboration status of the user in an electronic messaging system. By way of example, such embodiments may be extended to controlling the provision of notifications to other users and/or messages and notifications to the user.

Referring now to FIG. 6, there is depicted another embodiment of a system according to the invention comprising first 610 and second 615 health monitoring sensors. Here, the first sensor 610 is configured to detect the heart rate of a user of an electronic messaging system and to generate a first sensor output signal representative of the detected heart rate of the user. The second sensor 615 is configured to detect the blood pressure of the user and to generate a second sensor output signal representative of the detected blood pressure of the user.

The first 610 and second 615 health monitoring sensors are each configured to communicate their respective sensor output signals (e.g., signals indicating detected heart rate and blood pressure of the user) via the internet 620 (using a wired or wireless connection for example) to a remotely located data processing system 630 (such as server).

The data processing system 630 is configured to receive the sensor output signals from the first 610 and second 615 health monitoring sensors and process the received sensor output signals in accordance with a health status determination algorithm in order to determine an indicator of health of the user.

The data processing system 630 is also configured to retrieve information regarding the collaboration activity of the user. This may, for example, comprise the data processing system querying a user activity log/record of the electronic messaging system (which may for instance be provided by an application running in the data processing system), so as to obtain information relating to the user's recent collaboration activities using the electronic messaging system. The information may, for example, comprise: a number of messages sent by the user; a number of unread messages; a number of active or open discussions; and a number of draft messages. Using the obtained information regarding collaboration activity of the user, the data processing system is configured to determine an indicator of well-being (or indicator of stress) of the user.

Based on the determined indicator of health of the user and the determined indicator of well-being of the user the data processing system 630 then determines a current value of the collaboration status of the user.

The data processing system 630 is further configured to processes the current value of the collaboration status of the user in combination with historical data relating to one or more previously determined collaboration statuses of the user to determine a trend or pattern in the collaboration status over time. A trend can be found as a linear line (e.g., using linear regression), but may also be curved using higher order fitting techniques. A pattern can be found as a repeating pattern with respect to particular scale of time (e.g., day or week) for example.

The data processing system 630 is further configured to generate output signals representative of an inferred or determined collaboration status trend. Thus, the data processing system 630 provides a centrally accessible processing resource that can receive information from the health monitoring sensors 610, 615 and collaboration tools/applications and run one or more algorithms to transform the received information into a description of a trend or pattern in a collaboration status of the user.

Previously determined collaboration status values (and associated information, such as time, date, description, etc.) may therefore be stored, in a historical database for example, and then used in subsequent calculations. Furthermore, a currently determined collaboration status may be used to re-calculate or refine a previously determined trend or pattern. Thus, a pattern or trends of collaboration status of the user may be stored. Shifts in this pattern may indicate that the person is in need of help or assistance. For example, the person may start to become overworked, and this may be inferred from a trend in a collaboration status movement to a particular value (e.g., unavailable).

Further, the data processing system 630 is configured to detect an irregularity in the historical database. For example, by adding time information to the determined collaboration status values, the time spent between the changes in collaboration status may be determined. With the time information, the frequency of the changes may be determined. An irregularity in the historical database may then, for example, be that the time elapsed between the changes in collaboration status has increased.

Such provision of information about a detected or inferred collaboration status trend and/or irregularity may be undertaken in response to a receiving request (via the internet 620 for example) and/or may be undertaken without request (i.e. 'pushed').

For the purpose of receiving information about a detected collaboration status from the data processing system 630, and thus to enable the user to be monitored, the system further comprises first 640 and second 650 mobile computing devices.

Here, the first mobile computing device 640 is a mobile telephone device (such as a smartphone) with a display for displaying graphical elements representative of a person's physical or mental well-being. The second mobile computing device 650 is a mobile computer such as a Laptop or Tablet computer with a display for displaying graphical elements representative of a person's collaboration status.

The data processing system 630 is configured to communicate output signals to the first 640 and second 650 mobile computing devices via the internet 620 (using a wired or wireless connection for example). As mentioned above, this may be undertaken in response to receiving a request from the first 640 or second 650 mobile computing devices.

Based on the received output signals, the first 640 and second 650 mobile computing devices are configured to display one or more graphical elements in a display area provided by their respective display. For this purpose, the first 640 and second 650 mobile computing devices each comprise a software application for processing, decrypting and/or interpreting received output signals in order to determine how to display graphical elements. Thus, the first 640 and second 650 mobile computing devices each comprise a processing arrangement configured to one or more values representative of a trend or pattern, and to generate a display control signal for modifying at least one of the size, shape, position, orientation, pulsation or colour of the graphical element based on the one or more values representative of trend or pattern.

The system can therefore communicate information about a determined collaboration status of a user of an electronic messaging system to users of the first 640 and second 650 mobile computing devices. For example, each of the first 640 and second 650 mobile computing devices may be used to display graphical elements to a supervisor, colleague or manager. Also, the system can generate a warning signal in response to a detected irregularity. The irregularity may, for example, indicate that the user is in need of help and thus a generated alert or warning signal may be provided to at least one of: the user; a colleague; and a supervisor.

Implementations of the system of FIG. 6 may vary between: (i) a situation where the data processing system 630 communicates display-ready collaboration status data, which may for example comprise display data including graphical elements (e.g., in JPEG or other image formats) that are simply displayed to a user of a mobile computing device using conventional image or webpage display (which can be web based browser etc.); to (ii) a situation where the data processing system 630 communicates raw data set information that the receiving mobile computing device then processes to determine a trend or pattern in a user's collaboration status, and then displays graphical elements based on the determined trend or pattern (for example, using local software running on the mobile computing device). Of course, in other implementations, the processing may be shared between the data processing system 260 and a receiving mobile computing device such that part of the data generated at data processing system 630 is sent to the mobile computing device for further processing by local dedicated software of the mobile computing device. Embodiments may therefore employ server-side processing, client-side processing, or any combination thereof.

Further, where the data processing system 630 does not 'push' information (e.g., output signals), but rather communicates information in response to receiving a request, the user of a device making such a request may be required to confirm or authenticate their identity and/or security credentials in order for the information to be communicated.

In some embodiments, there may be provided a system comprising a processing arrangement configured to carry out any method previously described with reference to FIGS. 1 to 6.

Figure 7:
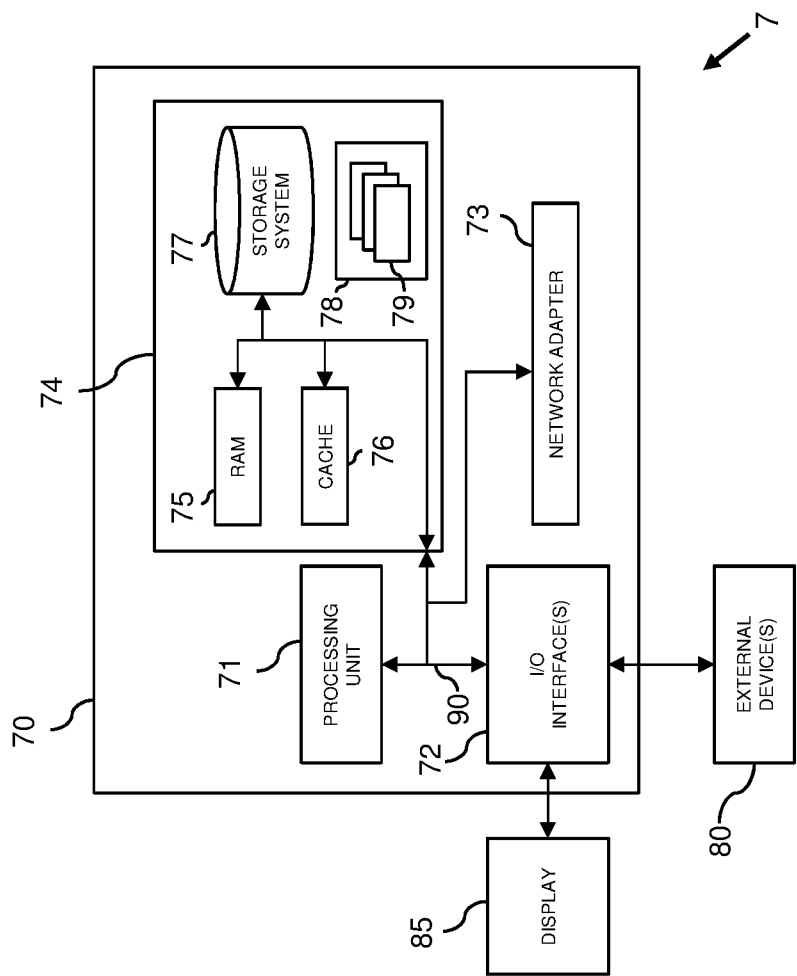
FIG. 7 illustrates a system for determining a collaboration status of a user of an electronic messaging system according to an embodiment.

By way of example, as illustrated in FIG. 7, embodiments may comprise a computer system 70, which may form part of a networked system 7. The components of computer system/server 70 may include, but are not limited to, one or more processing arrangements, for example comprising processors or processing units 71, a system memory 74, and a bus 90 that couples various system components including system memory 74 to processing unit 71.

Bus 90 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 70 typically includes a variety of computer system readable media. Such media may be any available media that is accessible by computer system/server 70, and it includes both volatile and non-volatile media, removable and non-removable media.

System memory 74 can include computer system readable media in the form of volatile memory, such as random access memory (RAM) 75 and/or cache memory 76. Computer system/server 70 may further include other removable/non-removable, volatile/non-volatile computer system storage media. By way of example only, storage system 77 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 90 by one or more data media interfaces. As will be further depicted and described below, memory 74 may include at least one program product having a set (e.g., at least one) of program modules that are configured to carry out the functions of embodiments of the invention.

Program/utility 78, having a set (at least one) of program modules 79, may be stored in memory 74 by way of example, and not limitation, as well as an operating system, one or more application programs, other program modules, and program data. Each of the operating system, one or more application programs, other program modules, and program data or some combination thereof, may include an implementation of a networking environment. Program modules 79 generally carry out the functions and/or methodologies of embodiments of the invention as described herein.

Computer system/server 70 may also communicate with one or more external devices 80 such as a keyboard, a pointing device, a display 85, etc.; one or more devices that enable a user to interact with computer system/server 70; and/or any devices (e.g., network card, modem, etc.) that enable computer system/server 70 to communicate with one or more other computing devices. Such communication can occur via Input/Output (I/O) interfaces 72. Still yet, computer system/server 70 can communicate with one or more networks such as a local area network (LAN), a general wide area network (WAN), and/or a public network (e.g., the Internet) via network adapter 73. As depicted, network adapter 73 communicates with the other components of computer system/server 70 via bus 90. It should be understood that although not shown, other hardware and/or software components could be used in conjunction with computer system/server 70. Examples, include, but are not limited to: microcode, device drivers, redundant processing units, external disk drive arrays, RAID systems, tape drives, and data archival storage systems, etc.

In the context of the present application, where embodiments of the present invention constitute a method, it should be understood that such a method is a process for execution by a computer, i.e. is a computer-implementable method. The various steps of the method therefore reflect various parts of a computer program, e.g., various parts of one or more algorithms.

The present invention may be a system, a method, and/or a computer program product. The computer program product may include a computer readable storage medium (or media) having computer readable program instructions thereon for causing a processor to carry out aspects of the present invention.

It will be appreciated that the embodiments described above and illustrated in the drawings represent only a few of the many ways of implementing embodiments for determining a collaboration status of a user in an automated manner. Present invention embodiments are not limited to the specific tasks or algorithms described above, but may be utilized for any system in which health information/mental engagement or status information is combined with user collaboration activity data to determine a user's collaboration status.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a storage class memory (SCM), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method, in an electronic messaging system comprising at least one processor and at least one memory, the at least one memory comprising instructions executed by the at least one processor to cause the at least one processsor to determine a collaboration status of a user, the method comprising:
   obtaining current health data representative of a physiological parameter or physical activity of the user;
   obtaining current collaboration activity data representative of social collaboration activity including workload of the user;
   determining a level of stress of the user based on the obtained current health data and the current collaboration activity data;
   obtaining one or more of historical health data and historical collaboration activity data of the user, and detecting one or more patterns of collaboration status of the user based on the one or more of historical health data and historical collaboration activity data;
   refining the detected one or more patterns of collaboration status based on the one or more of historical health data and historical collaboration activity data, according to the current health data and current collaboration data; and
   determining the collaboration status indicating availability of the user based on the determined level of stress from the current health data and collaboration activity data, the one or more patterns of collaboration status of the user, and the refined one or more patterns of collaborative status.

2. The method of claim 1, further comprising:
obtaining historical health data relating to a pattern or trend of previously obtained measurements of a physiological parameter or physical activity of the user,
and wherein the collaboration status of the user is further based on the obtained historical health data.

3. The method of claim 2, further comprising:
associating the collaboration status with a future time or date based on the obtained historical health data in order to predict the collaboration status of the user for the future time or date.

4. The method of claim 1, wherein the physiological parameter or physical activity of the user comprises at least one of:
heart rate;
blood pressure;
body temperature;
pulse-oximetry;
hormone level;
mood;
steps taken; and
distance walked.

5. The method of claim 1, wherein the social collaboration activity of the user comprises at least one of:
number of meetings attended during a predetermined time period;
time spent in meetings during a predetermined time period;
distance traveled during a predetermined time period;
number of messages sent using the electronic messaging system during a predetermined time period;
number of words typed in messages sent using the electronic messaging system during a predetermined time period;
number of active parallel discussions using the electronic messaging system;
number of open draft messages or emails;
number of comments or articles submitted to an online community during a predetermined time period; and
number of unread electronic messages or emails.

6. The method of claim 1, further comprising:
obtaining historical collaboration activity data relating to a pattern or trend of previously obtained measurements of social collaboration activity of the user,
and wherein the collaboration status of the user is further based on the obtained historical collaboration activity data.

7. The method of claim 6, further comprising:
associating the collaboration status with a future time or date based on the obtained historical collaboration activity data in order to predict the collaboration status of the user for the future time or date.

8. The method of claim 1, further comprising:
obtaining a user input representative of a current or future collaboration status of the user,
and wherein the collaboration status of the user is further based on the obtained user input.

9. The method of claim 1, further comprising:
obtaining a message of the user communicated by the electronic messaging system; and
analyzing the message to identify an indicator of status of the user,
and wherein the collaboration status of the user is further based on the identified indicator of status of the user.

10. The method of claim 9, further comprising;
determining a time or date associated with the identified indicator of status of the user,
and wherein the collaboration status of the user is further based on the determining a time or date associated with the identified indicator of status of the user.

11. The method of claim 1, further comprising:
controlling communication of a notification associated with the user based on the collaboration status of the user.

12. The method of claim 11, further comprising:
obtaining historical information relating to a previous collaboration status of the user,
and wherein controlling communication of the notification associated with the user is further based on the obtained historical information.

* * * * *